United States Patent [19]

Effland et al.

[11] Patent Number: 4,789,678

[45] Date of Patent: Dec. 6, 1988

[54] MEMORY ENHANCING α-ALKYL-4-AMINO-3-QUINOLINEMETHANOLS AND 1-(4-ARALKYLAMINO-3-QUINOLINYL)ALKANONES AND RELATED COMPOUNDS

[75] Inventors: Richard C. Effland; Joseph T. Klein, both of Bridgewater, N.J.

[73] Assignee: Hoechst-Roussel Pharmaceuticals, Inc., Somerville, N.J.

[21] Appl. No.: 899,584

[22] Filed: Aug. 25, 1986

[51] Int. Cl.$^4$ .................. C07D 215/14; A61K 31/47
[52] U.S. Cl. .................... 514/313; 546/159; 558/414
[58] Field of Search ............. 514/313; 546/159

[56] References Cited

U.S. PATENT DOCUMENTS

| | | | |
|---|---|---|---|
| 2,785,165 | 3/1957 | Schock et al. | 546/159 |
| 4,180,670 | 12/1979 | Edington et al. | 546/284 |
| 4,631,286 | 12/1986 | Shutske et al. | 514/297 |
| 4,695,573 | 9/1987 | Shutske et al. | 514/290 |

FOREIGN PATENT DOCUMENTS

| | | | |
|---|---|---|---|
| 229393 | 8/1958 | Australia | 546/156 |
| 56766 | 7/1982 | European Pat. Off. | 546/159 |
| 179383 | 4/1986 | European Pat. Off. | |
| 43-20294 | 8/1968 | Japan | 546/159 |

OTHER PUBLICATIONS

Abstract for Japan Patent 43-20294 (8/31/68).
"A Survey of Antimalarial Drugs" (1941–1945), Frederick Y. Wiselogle (Editor), vol. II, Part 2, pp. 1047, etc. (1946).
Schäfer et al., J. Prakt. Chem., 321, pp. 695–698 (and English translation, pp. 1–5) (1979).
Hershenson et al., J. Med. Chem., 29, pp. 1125–1130 (1986).
Davies, Drug Development Research, 5, pp. 69–76 (1985).

Primary Examiner—Donald G. Daus
Assistant Examiner—E. Bernhardt
Attorney, Agent, or Firm—Tatsuya Ikeda

[57] ABSTRACT

There are described compounds of the formula

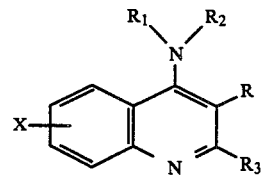

where X is hydrogen, halogen, loweralkyl, loweralkoxy or trifluoromethyl; R is

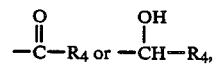

$R_4$ being loweralkyl; $R_1$ is hydrogen, loweralkyl or arylloweralkyl; $R_2$ is hydrogen, loweralkyl or arylloweralkyl; and $R_3$ is loweralkyl, with the proviso that when R is acetyl, $R_3$ is methyl and X is hydrogen, $R_1$ and $R_2$ are not both hydrogen, or pharmaceutically acceptable acid addition salts thereof, which are useful in the treatment of various memory dysfunctions characterized by decreased cholinergic function.

18 Claims, No Drawings

MEMORY ENHANCING α-ALKYL-4-AMINO-3-QUINOLINEMETHANOLS AND 1-(4-ARALKYLAMINO-3-QUINOLINYL)ALKANONES AND RELATED COMPOUNDS

There are described compounds of the formula

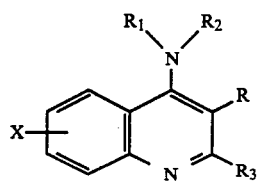

where X is hydrogen, halogen, loweralkyl, loweralkoxy or trifluoromethyl; R is

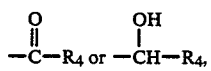

$R_4$ being loweralkyl; $R_1$ is hydrogen, loweralkyl or arylloweralkyl; $R_2$ is hydrogen, loweralkyl or arylloweralkyl; and $R_3$ is loweralkyl, with the proviso that when R is acetyl, $R_3$ is methyl and X is hydrogen, $R_1$ and $R_2$ are not both hydrogen, or pharmaceutically acceptable acid addition salts thereof, which are useful for enhancing memory and for treating Alzheimer's disease; pharmaceutical compositions comprising an effective memory enhancing amount of such a compound and a method of treating a patient in need of memory enhancement which comprises administering such a compound to the patient.

Unless otherwise stated or indicated, the following definitions shall apply throughout the specification and the appended claims.

The term loweralkyl shall mean a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

The term halogen shall mean fluorine, chlorine, bromine or iodine.

The term aryl shall mean an unsubstituted phenyl group or a phenyl group substituted with 1, 2 or 3 substituent groups each of which being independently loweralkyl, halogen, loweralkoxy, or trifluoromethyl.

Throughout the specification and appended claims a given chemical formula or name shall include all optical isomers and mixtures thereof where such isomers exist.

The compounds of this invention are prepared by utilizing one or more of the steps described below.

Throughout the description of the synthetic steps, the notations, X, R, $R_1$, $R_2$, $R_3$ and $R_4$ shall have the respective meanings given above unless otherwise stated or indicated.

STEP A

Anthranilonitrile is reacted with a diketone of formula II to afford an enamine of formula III.

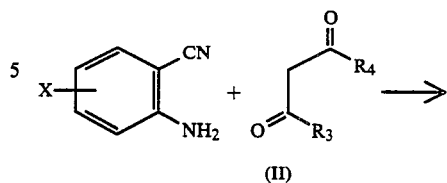

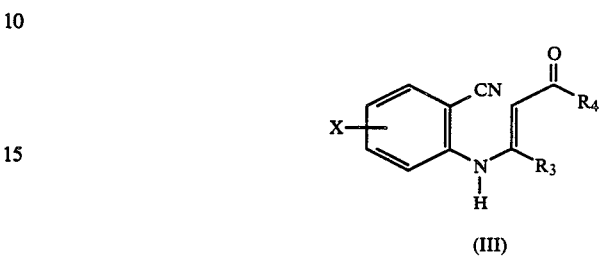

Said condensation reaction is typically conducted in the presence of a suitable acid catalyst such as p-toluenesulfonic acid and a solvent such as toluene and refluxing the reaction mixture for several hours. Synthesis of the compound of formula III corresponding to $R_3=R_4=$methyl is described in H. Schaefer et al., J. Prakt. Chemie, 321, 695–698 (1979). Where $R_3$ is not the same as $R_4$, the above reaction gives rise to two different products, but separation between them can be accomplished, for instance, by flash chromatography.

STEP B

Compound III is cyclized in the presence of sodium methoxide to afford a compound of formula IV.

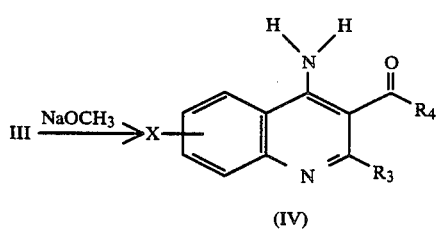

Said cyclization is typically conducted by first preparing a solution of sodium methoxide in methanol by a routine procedure and thereafter adding compound III (in neat form or as a methanol solution) to the sodium methoxide solution and gently refluxing the reaction mixture for about one hour or less. Synthesis of the compound of formula IV corresponding to $R_3=R_4=$methyl is also described in the above-mentioned Schaefer et al. article.

STEP C

Compound IV is reacted with a bromide compound of the formula $R_1$—Br ($R_1$ is not hydrogen) to afford a compound of formula V.

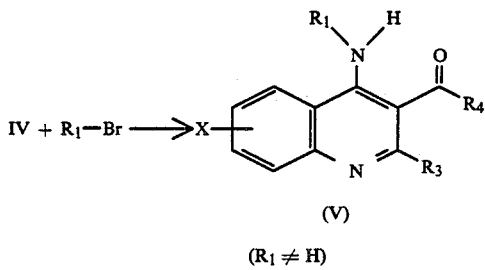

(V)

($R_1 \neq H$)

The above reaction is typically conducted by adding a solution of compound IV in a suitable solvent such as dimethylsulfoxide to a slurry prepared from pulverized potassium hydroxide and the same solvent, stirring the resultant mixture at room temperature for less than one hour, adding a solution of the bromide compound in the solvent, and stirring the resultant mixture at room temperature for several hours.

STEP D

Compound V is allowed to react with a bromide compound of the formula $R_2$—Br ($R_2$ is not hydrogen) in substantially the same manner as in STEP C to afford a compound of formula VI.

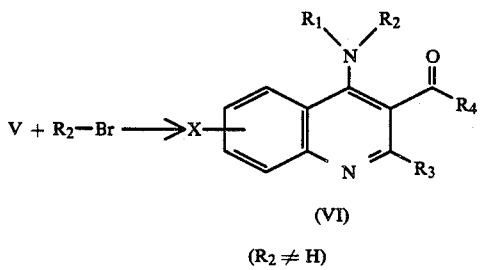

(VI)

($R_2 \neq H$)

When $R_2$ is identical to $R_1$, it is usually not necessary to conduct STEP D separately from STEP C. Namely, the di N-substituted compound is obtained in the same reaction system along with the mono N-substituted compound while conducting STEP C. Separation between the mono and di N-substituted compound can be accomplished, for instance, by flash chromatography using gradient elution of dichloromethane and gradually increasing amounts of ethyl acetate.

STEP E

A compound of formula VI where $R_1$ and $R_2$ may be hydrogen, loweralkyl or arylloweralkyl which is obtained from STEP C, D or E above is reduced with sodium borohydride to afford a compound of formula VII.

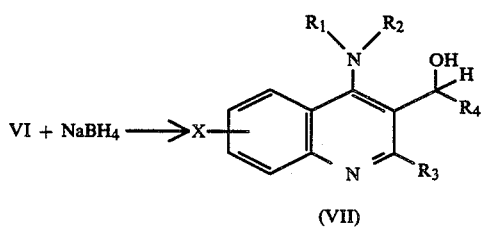

(VII)

The above reduction is typically conducted in a suitable medium such as isopropanol, ethanol, methanol or the like and stirring the reaction mixture at a temperature between ambient temperature and reflux temperature of the reaction mixture.

The compounds of formula (I) of the present invention are useful in the treatment of various memory dysfunctions characterized by decreased cholinergic function, such as Alzheimer's disease. This utility is demonstrated by the ability of these compounds to restore cholinergically deficient memory in the Dark Avoidance Assay.

Dark Avoidance Assay

In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animals's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment. The results of some of the compounds of this invention are presented in Table 1.

TABLE 1

| | Dark Avoidance Assay | |
|---|---|---|
| Compound | Dose (mg/ kg of Body Weight) | % of Animals With Scopolamine Induced Memory Deficit Reversed |
| 4-amino-α, 2-dimethyl-3-quinolinemethanol | 2.5 | 50 |
| 4-amino-α-ethyl-2-methyl-3-quinoline-methanol | 1.25 | 20 |
| 1-(4-amino-2-methyl-3-quinolinyl)propanone (prior art compounds) | 0.16 | 73 |
| Tacrine | 0.63 | 13 |
| Pilocarpine | 1.25 | 19 |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:
4-amino-α,2-dimethyl-3-quinolinemethanol;
1-(4-benzylamino2-methyl-3-quinolinyl)-ethanone;
4-benzylamino-α,2-dimethyl-3-quinolinemethanol;
1-[4-(4-fluorophenylmethyl)amino-2-methyl-3-quinolinyl]-ethanone;
1-[4-(2-fluorophenylmethyl)amino 2-methyl-3-quinolinyl]-ethanone;
1-[4-bis(2-fluorophenylmethyl)amino-2-methyl-3-quinolinyl]-ethanone;
1-(4-amino-2-methyl-3-quinolinyl)-propanone;
4-amino-α-ethyl-2-methyl-3-quinolinemethanol;
1-(4-amino-2-ethyl-3-quinolinyl)-ethanone; and
4-benzylamino-α-ethyl-2-methyl-3-quinolinemethanol.

The following examples are given for the purpose of illustrating this invention.

EXAMPLE 1

1-(4-Amino-2-methyl-3-quinolinyl)-ethanone

A solution prepared from 11.81 g of anthranilonitrile, 15 g of 2,4-pentanedione, about 0.15 g of p-benzenesulfonic acid and 200 ml of toluene was stirred for 12 hours at reflux, cooled and concentrated to give about 15.5 g of crystals. The crystals were dried in a vacuum oven at room temperature to give 13.9 g of the desired enamine, m.p. 105° C., some prior softening.

Sodium metal (0.75 g) was dissolved in 30 ml of anhydrous methanol. After the formation of sodium methoxide, 6 g of the enamine was added to the solution. After about 45 minutes of gentle reflux, the reaction mixture was cooled, about 2 ml of water was added and most of the methanol was removed by evaporation. The resultant mixture was stirred with water and extracted with ethyl acetate. The extract was dried over anhydrous magnesium sulfate and concentrated to give 7.5 g of the cyclized product. Recrystallization from benzene gave 4.3 g of a solid. Purification of this material by flash chromatography followed by sublimation gave an analytically pure sample melting at 159°–160° C.

EXAMPLE 2

4-Amino-α,2-dimethyl-3-quinolinemethanol 1-(4-amino-2-methyl-3-quinolinyl)-ethanone (2 g) was added all at once as a solid to a stirred suspension of sodium borohydride (1.13 g) in isopropanol (50 ml). The mixture was refluxed for several hours until the reaction was complete based on thin-layer chromatography (silica gel, 10% methanol/dichloromethane). Methanol (10 ml) and water (5 ml) were added and the mixture was allowed to cool slowly to room temperature. Most of the solvent was evaporated under vacuum, and the concentrate partitioned between water and ethyl acetate. The ethyl acetate extract was dried (saturated sodium chloride wash, sodium sulfate) and the ethyl acetate removed under vacuum. The resulting solid was recrystallized from acetonitrile to give 1.5 g of crystals, mp 214°.

| ANALYSIS: | | | |
|---|---|---|---|
| Calculated for $C_{12}H_{14}N_2O$: | 71.24% C | 6.99% H | 13.85% N |
| Found: | 71.06% C | 6.87% H | 13.48% N |

EXAMPLE 3

1-(4-Benzylamino-2-methyl-3-quinolinyl)-ethanone hydrochloride

To a solution of 1-(4-amino-2-methyl-3-quinolinyl)-ethanone (9 g) in 80 ml of dimethylsulfoxide was added powdered 85% potassium hydroxide (3.6 g). After thirty minutes, benzyl bromide (9 g) was slowly added. After four hours of stirring at ambient temperature, the reaction mixture was stirred with 80 ml of water and extracted with ether. The organic extract was washed with water and saturated sodium chloride, dried over anhydrous sodium sulfate, filtered and evaporated to 16.4 g of oil. This oil was purified by HPLC (high performance liquid chromatography) (silica, 20% ethyl acetate in dichloromethane) to give 5.9 g of the desired product as a solid, mp 99°–100°. A 2.2 g portion was dissolved in 25 ml of warm isopropanol, filtered and converted to the hydrochloride salt by the addition of ethereal hydrochloric acid. The crystals which formed upon cooling were collected and dried to give 2.2 g of solid, d 242°–243°. This material was recrystallized from ethanol/ether to give 2.0 g of crystals, d 242°–243°.

| ANALYSIS: | | | |
| --- | --- | --- | --- |
| Calculated for $C_{19}H_{18}N_2O\cdot HCl$: | 69.82% C | 5.86% H | 8.57% N |
| Found: | 69.63% C | 5.99% H | 8.54% N |

EXAMPLE 4

4-Benzylamino-α,2-dimethyl-3-quinolinemethanol

A solution prepared from 1-(4-benzylamino-2-methyl-3-quinolinyl)-ethanone (4 g), sodium borohydride (1 g), 75 ml of isopropanol and 25 ml of methanol was stirred one hour at 45°, cooled, stirred with 500 ml of water and extracted with dichloromethane. The organic extract was washed with water and saturated sodium chloride and dried over anhydrous sodium sulfate, filtered and evaporated to 4 g of solid. This material was purified by flash chromatography (silica, 10% methanol in dichloromethane) to give 3.6 g of solid, mp 176°–177°.

| ANALYSIS: | | | |
| --- | --- | --- | --- |
| Calculated for $C_{19}H_{20}N_2O$: | 78.05% C | 6.90% H | 9.58% N |
| Found: | 78.11% C | 6.92% H | 9.64% N |

EXAMPLE 5

1-[4-(4-fluorophenylmethyl)amino-2-methyl-3-quinolinyl]-ethanone hydrochloride

A solution of 1-(4-amino-2-methyl-3-quinolinyl)-ethanone (10 g) in dimethylsulfoxide (80 ml) was added to a slurry of powdered 85% potassium hydroxide (3.5 g) in dimethylsulfoxide (20 ml). This mixture was stirred for fifteen minutes, and a solution of 4-fluorobenzyl bromide (9.9 g) in dimethylsulfoxide (20 ml) was added dropwise. After stirring at ambient temperature for 2.5 hours, the reaction mixture was poured onto ice/water and extracted with dichloromethane. The organic extract was washed with water, saturated sodium chloride and dried over sodium sulfate. Removal of the sodium sulfate by filtration and the solvent by evaporation gave 16 g of tacky oil. Approximately 13 g was chromatographed via flash chromatography with ether as eluent to give 5 g of pure solid, mp 92°–96°.

The hydrochloride salt was prepared by dissolving 3 g of the solid in absolute ethanol, adding ethereal/hydrochloric acid and diluting the mixture with ether. On stirring at room temperature, a white solid formed which was filtered, washed with absolute ethanol/ether and dried to give 2.7 g of product, mp 222°–224°.

| ANALYSIS: | | | |
| --- | --- | --- | --- |
| Calculated for $C_{19}H_{17}FN_2O\cdot HCl$: | 66.17% C | 5.27% H | 8.12% N |
| Found: | 65.73% C | 5.24% H | 7.98% N |

EXAMPLE 6

1-[4-(2-fluorophenylmethyl)amino-2-methyl-3-quinolinyl]-ethanone

A solution of 1-(4-amino-2-methyl-3-quinolinyl)-ethanone in dimethylsulfoxide (150 ml) was added to a stirred slurry of pulverized 85% potassium hydroxide (7 g) in dimethylsulfoxide (40 ml). This mixture was stirred at ambient temperature for twenty minutes, and thereafter a solution of o-fluorobenzylchloride (15.2 g) in dimethylsulfoxide (40 ml) was added dropwise. The mixture was stirred for two hours and allowed to stand overnight at room temperature. Thereafter, it was poured onto ice and diluted with water to form a tacky lump. This was allowed to stand for fifteen minutes, and the aqueous dimethylsulfoxide was decanted. The tacky precipitate was dissolved in dichloromethane, washed with water (3x) and saturated sodium chloride solution, and dried over sodium sulfate. Removal of the sodium sulfate by filtration and the solvent by evaporation gave 26.5 g of viscous oil.

Flash chromatography using gradient elution of dichloromethane and gradually increasing amounts of ethyl acetate gave a sufficient separation to enable the purification and identification of three major components: the mono, di and tri N-benzylated products. From various fractions collected, 8.6 g of mono N-benzylated product was isolated. Recrystallization of 4.5 g portion from ether/petroleum ether gave 3.4 g of solid, mp 19°–120°.

| ANALYSIS: | | | |
| --- | --- | --- | --- |
| Calculated for $C_{19}H_{17}FN_2O$: | 74.00% C | 5.57% H | 9.10% N |
| Found: | 74.12% C | 5.70% H | 9.12% N |

EXAMPLE 7

1-[4-bis(2-fluorophenylmethyl)amino-2-methyl-3-quinolinyl]-ethanone

A solution of 1-(4-amino-2-methyl-3-quinolinyl)-ethanone in dimethylsulfoxide (150 ml) was added to a stirred slurry of pulverized 85% potassium hydroxide (7 g) in dimethylsulfoxide (40 ml). This mixture was stirred at ambient temperature for twenty minutes, and thereafter a solution of o-fluorobenzylchloride (15.2 g) in dimethylsulfoxide (40 ml) was added dropwise. The mixture was stirred for two hours and allowed to stand overnight at room temperature. Thereafter, it was then poured onto ice and diluted with water to form a tacky lump. This was allowed to stand for fifteen minutes, and the aqueous dimethylsulfoxide was decanted. The tacky precipitate was dissolved in dichloromethane, washed with water (3×) and saturated sodium chloride solution, and dried over sodium sulfate. Removal of the sodium sulfate by filtration and the solvent by evaporation gave 26.5 g of viscous oil.

Flash chromatography using gradient elution of dichloromethane and gradually increasing amounts of ethyl acetate gave a sufficient separation to enable the purification and identification of three major components: the mono, di and tri N-benzylated products. The N,N-dibenzylated product was obtained as 2.5 g of oil which solidified on standing. Recrystallization from ether/petroleum ether gave 1.6 g of solid, mp 102°–103°.

| ANALYSIS: | | | |
|---|---|---|---|
| Calculated for $C_{26}H_{22}F_2N_2O$: | 74.97% C | 5.33% H | 6.73% N |
| Found: | 74.60% C | 5.27% H | 6.68% N |

EXAMPLE 8

1-(4-Amino-2-methyl-3-quinolinyl)-propanone

A solution prepared from anthranilonitrile (26 g), 2,4-hexanedione (25 g), 0.2 g of p-toluenesulfonic acid and 400 ml of toluene was stirred four hours at reflux, cooled and evaporated to 48 g of oil. This oil was purified by HPLC (silica, dichloromethane) to give 29 g of the major enamine isomer as an oil.

Sodium metal (3.5 g) was dissolved in 200 ml of methanol. To the freshly prepared sodium methoxide was added a solution of the enamine (29 g) in 100 ml of methanol. After stirring at reflux for thirty minutes, the reaction mixture was cooled, evaporated, stirred with water and extracted with ethyl acetate. The organic extract was washed with water and saturated sodium chloride, dried over anhydrous sodium sulfate, filtered and evaporated to 27 g of waxy residue. This material was purified by HPLC (silica, ethyl acetate) to give 18 g of solid, mp 130°–133°. A six gram sample was purified by flash chromatography (silica, 25% dichloromethane/ethyl acetate) to give 3.2 g of solid, mp 139°–140°. This material was recrystallized from isopropyl ether/petroleum ether to give 2.3 g of crystals, mp 140°–141°. This material was sublimed at 120°–130°/0.01 mmHg to give 2.0 g of crystals, mp 140°–142°.

| ANALYSIS: | | | |
|---|---|---|---|
| Calculated for $C_{13}H_{14}N_2O$: | 72.87% C | 6.59% H | 13.08% N |
| Found: | 72.97% C | 6.64% H | 13.25% N |

EXAMPLE 9

4-Amino-α-ethyl-2-methyl-3-quinolinemethanol

A mixture prepared from 1-(4-amino-2-methyl-3-quinolinyl)-propanone (8 g), sodium borohydride (3 g), 75 ml of isopropanol and 25 ml of methanol was stirred twenty hours at ambient temperature. The reaction mixture was concentrated and stirred with water, and the product which separated was collected and dried to 8 g of solid, mp 220°–230°. This material was recrystallized from absolute ethanol to give 4.6 g of crystals, mp 240°–241°.

| ANALYSIS: | | | |
|---|---|---|---|
| Calculated for $C_{13}H_{16}N_2O$: | 72.19% C | 7.46% H | 12.96% N |
| Found: | 72.04% C | 7.48% H | 12.91% N |

EXAMPLE 10

1-(4-Amino-2-ethyl-3-quinolinyl)-ethanone

A solution prepared from anthranilonitrile (26 g), 2,4-hexanedione (25 g), 0.2 g of p-toluenesulfonic acid and 400 ml of toluene was stirred four hours at reflux, cooled and evaporated to 48 g of oil. This oil was purified by HPLC (silica, dichloromethane) to give 29 g of the major enamine isomer as an oil and 1.9 g of the minor enamine isomer as an oil.

Sodium metal (0.25 g) was dissolved in 50 ml of methanol. To the freshly prepared sodium methoxide was added a solution of the minor enamine isomer (1.8 g) in 10 ml of methanol. After thirty minutes of stirring at reflux, the reaction mixture was cooled, evaporated, stirred with water and extracted with dichloromethane. The organic extract was washed with water and saturated sodium chloride, dried over anhydrous sodium sulfate, filtered and evaporated to 1.6 g of solid. This material was purified by flash chromatography (silica, 50% ethyl acetate/dichloromethane) to give 1.1 g of solid, mp 145°–148°. A 200 mg sample was sublimed at 135°–145°/0.01 mmHg to give 150 mg of crystals, mp 148°–150°.

| ANALYSIS: | | | |
|---|---|---|---|
| Calculated for $C_{13}H_{14}N_2O$: | 72.87% C | 6.59% H | 13.08% N |
| Found: | 72.87% C | 6.66% H | 13.10% N |

We claim:

1. A compound having the formula

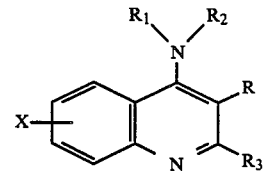

where X is hydrogen, halogen, loweralkyl, loweralkoxy or trifluoromethyl; R is

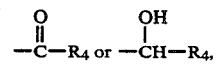

$R_4$ being loweralkyl; $R_1$ is hydrogen, loweralkyl or phenylloweralkyl in which the phenyl group may be substituted with 1,2 or 3 substituents consisting of the following: loweralkyl, halogen, loweralkoxy, or trifluoromethyl; $R_2$ is hydrogen, loweralkyl or phenylloweralkyl in which the phenyl group may be substituted with 1,2 or 3 substituents consisting of the following: loweralkyl, halogen, loweralkoxy, or trifluoromethyl; and $R_3$ is loweralkyl, with the proviso that when R is acetyl, $R_3$ is methyl and X is hydrogen, $R_1$ and $R_2$ are not both hydrogen, or a pharmaceutically acceptable acid addition salt thereof.

2. The compound as defined in claim 1, where R is

3. The compound as defined in claim 1, where R is

$R_1$ is hydrogen and $R_2$ is arylloweralkyl.

4. The compound as defined in claim 1, where R is

R₁ is arylloweralkyl and R₂ is arylloweralkyl.

5. The compound as defined in claim 1, where R is

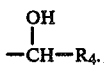

6. The compound as defined in claim 1, where R is

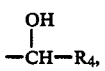

R₁ is hydrogen and R₂ is arylloweralkyl.

7. The compound as defined in claim 1, where R is

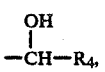

R₁ is arylloweralkyl and R₂ is arylloweralkyl.

8. The compound as defined in claim 1, which is 4-amino-α,2-dimethyl-3-quinolinemethanol.

9. The compound as defined in claim 1, which is 1-(4-benzylamino-2-methyl-3-quinolinyl)-ethanone.

10. The compound as defined in claim 1, which is 4-benzylamino-α,2-dimethyl-3-quinolinemethanol.

11. The compound as defined in claim 1, which is 1-[4-(4-fluorophenylmethyl)amino-2-methyl-3-quinolinyl]-ethanone.

12. The compound as defined in claim 1, which is 1-[4-(2-fluorophenylmethyl)amino-2-methyl-3-quinolinyl]-ethanone.

13. The compound as defined in claim 1, which is 1-[4-bis(2-fluorophenylmethyl)amino-2-methyl-3-quinolinyl]-ethanone.

14. The compound as defined in claim 1, which is 1-(4-amino-2-methyl-3-quinolinyl)-propanone.

15. The compound as defined in claim 1, which is 4-amino-α-ethyl-2-methyl-3-quinolinemethanol.

16. The compound as defined in claim 1, which is 1-(4-amino-2-ethyl-3-quinolinyl)-ethanone.

17. The compound as defined in claim 1, which is 4-benzylamino-α-ethyl-2-methyl-3-quinolinemethanol.

18. A pharmaceutical composition comprising an effective memory enhancing amount of a compound as defined in claim 1 and a suitable carrier therefor.

* * * * *